United States Patent [19]

Huang

[11] Patent Number: 5,047,505

[45] Date of Patent: Sep. 10, 1991

[54] **HIGH LEVEL EXPRESSION IN *E COLI* OF SOLUBLE MATURE HIL-1BETA AND DERIVATIVES WITH ALTERED BIOLOGICAL ACTIVITY**

[75] Inventor: James J. Huang, Wallingford, Pa.

[73] Assignee: Du Pont Merck Pharmaceutical Company, Wilmington, Del.

[21] Appl. No.: 132,185

[22] Filed: Dec. 18, 1987

Related U.S. Application Data

[63] Continuation-in-part of Ser. No. 6,870, Jan. 27, 1987, abandoned.

[51] Int. Cl.$^5$ ................ C07K 15/06; C07K 13/00
[52] U.S. Cl. ................ 530/351; 435/69.52; 435/172.3; 935/10; 536/27
[58] Field of Search ............... 435/68, 172.3, 320, 435/252.33; 530/351

[56] References Cited

U.S. PATENT DOCUMENTS 4,468,464  8/1984  Cohen et al. ............... 435/317

FOREIGN PATENT DOCUMENTS 0161901  11/1985  European Pat. Off. .
0165654  12/1985  European Pat. Off. .
0187991  1/1987   European Pat. Off. .
0237967  4/1990   European Pat. Off. .

OTHER PUBLICATIONS

Mosley et al., *Proceedings, National Academy Science, U.S.A.*, vol. 84, pp. 4572–4576, Jul. 1987.
Horuk, et al., *Journal of Biological Chemistry*, vol. 262, No. 34, pp. 16275–16278, 1987.
Clark-Lewis et al. 1986, *Science*. 231, 134–139.
March et al., *Nature*, 315:641–647, 20 Jun. 1985.
Kronheim et al., *Biotechnology*, 4:1078–1082, Dec. 1986.
Auron et al., *Proc. Natl. Acad. Sci., U.S.A.*, 81:7907–7911 (1984).
Dinarello et al., *J. Clin. Invest.*, 77:1734–1739 (Jun. 1986).
Rossenwasser et al., *Proc. Natl. Acad. Sci., U.S.A.*, 83:5243–5246 (Jul. 1987).
Gubler et al., *J. Immunology*, 136:2492–2497 (1986).
Vieira et al., *Gene*, 19:259–268 (1982).
Catalog of Pharmacia Laboratories of Piscataway, N.J., pp. 60, 136 & 139.
Thornton, et al., *J. Mol. Biol.* (1963):167, 443–460.
Oppenheim, et al., *Immunology Today*, vol. 7, No. 2, pp. 45–56.
Bachmair, et al., *Science*, vol. 34, pp. 179–186 (1986).
Killian et al., *J. Immunology*, vol. 136, No. 12, pp. 4509–4514 (1986).
Dower, et al., *Nature*, vol. 324, pp. 266–268.
Wingfield, et al., *Eur. J. Biochem*, 160:491–497 (1986).
Meyers et al., *J. Biol. Chem.*, vol. 62, No. 23, pp. 11176–11181 (1987).
Tocci, et al., *J. Immunology*, vol. 138, pp. 1109–1114 (1987).
Dinarello, *Bull. Inst. Pasteur*, 1987:85, 267–285.
Dinarello, *FASEB J.*, vol. 2, 108–115 (1988).
Mosley, et al., *Proc. Natl. Acad. Sci., U.S.A.*, vol. 84, pp. 4572–4576 (Jul. 1987).
Vierra et al. (1982) *Gene* 19, 259–268.
March et al. (1985) *Nature* 315, 614–647.
Int. Biotech. Inc. Catalog (1986–1987) pp. 117–120.
Wingfield et al. (1986) *Eur. J. Biochem.* 160, 491–497.
Auron et al. (1984) *Proc. Natl. Acad. Sci.* U.S.A. 84, 7907–7911.
Thornton et al. (1983) 167, 443–460.
Bachmair et al. (1986) *Science* 34, 179–186.
Huang et al., *FEBS Letters*, vol. 223, No. 2, Nov. 2, 1987, pp. 294–298.
Huang, et al., *Mol. Biol. Med.* (1974), vol. 4, pp. 169–181.

*Primary Examiner*—Elizabeth C. Weimar
*Assistant Examiner*—Christopher Low

[57] ABSTRACT

Plasmid pUC8 and DNA coding for hIL-1β are used to construct hybrid plasmids capable of high level expression in *E. coli* of soluble proteins, including mature hIL-1β and derivatives of mature hIL-1β having amino acid substitutions and insertions at one or all of positions 1 to 4 at the amino terminus. Derivatives of hIL-1β with alterations at the N-terminus have been produced which have either enhanced or decreased bioactivity compared to native monocyte derived hIL-1β.

1 Claim, 3 Drawing Sheets

FIG. 1 pcD1218
  ↓   BamHI 1.6 Kb BamHI
Restriction Fragment
Encoding pro hIL-1β

↓   pUC9/BamHI pUC9 - pro hIL-1β

↓   Acc I pUC9 - pro hIL-1βΔAccI

↓   HgiAI/PstI 0.6 Kb HgiAI/PstI
Restriction Fragment
Encoding mature hIL-1β

↓   pUC8/PstI pDP506

↓   EcoRI/SalI
      Bal 31 pDP516 pDP516-16
pDP516-18
pDP516-22A
pDP516-23

```
        BamHI        HgiAI           AccI              BamHI
        ├────────────┼───────────────┼─────────────────┤
        1            348/351         807

FIG. 2   pcD1218/BamHI
```

```
               HgiAI          1                    153              PstI
               ├──┤           │117              269│                ├──┤
    ... GCT TAT GTG CAC GAT GCA CCT GTA CGA TCA ... TCC TAA ... CTG CAG
        Ala Tyr Val His Asp Ala Pro Val Arg Ser ... Ser end FIG. 3   pUC9-hIL-1βΔAccI
```

```
                              EcoRI  SmaI  BamHI
                              ├──┤   ├──┤  ├──┤
    ... ATG ACC ATG ATT ACG AAT TCC CGG GGA TCC -
        Thr Met Ile Thr Asn Ser Arg Gly Ser -

SalI    PstI      HindIII
        ├──┤    ├──┤      ├──┤
        GTC GAC CTG CAG CCA AGC TTG GCA CTG GCC
        Val Asp Leu Gln Pro Ser Leu Ala Leu Ala FIG. 4   pUC8
```

```
                              EcoRI SmaI BamHI
                              ├──┤  ├──┤ ├──┤
    ... ATG ACC ATG ATT ACG AAT TCC CGG GGA TCC -
        Thr Met Ile Thr Asn Ser Arg Gly Ser -

SalI              1                    153
        ├──┤              │117              269│
        GTC GAC CTG CAC GAT GCA CCT GTA CGA TCA ... TCC TAA ...
        Val Asp Leu His Asp Ala Pro Val Arg Ser ... Ser end FIG. 5   pDP506
```

```
                  1                           153
                117                           269
... ATG ACC AAT GCA CCT GTA CGA TCA ... TCC TAA ...
    Thr Asn Ala Pro Val Arg Ser ... Ser end FIG. 6  pDP516
```

```
                  1                           153
                117                           269
... ATG ACA CCT GTA CGA TCA ... TCC TAA ...
    Thr Pro Val Arg Ser ... Ser end FIG. 7  pDP516-22A
```

```
                  1                           153
                117                           269
... ATG ACC ATG GTA CGA TCA ... TCC TAA ...
    Thr Met Val Arg Ser ... Ser end FIG. 8  pDP516-18
```

```
                  1                           153
                117                           269
... ATG ACC ATC GAT GCA CCT GTA CGA TCA ... TCC TAA ...
    Thr Ile Asp Ala Pro Val Arg Ser ... Ser end FIG. 9  pDP516-23
```

```
                  1                           153
                117                           269
... ATG ACC CTG CAC GAT GCA CCT GTA CGA TCA ... TCC TAA ...
    Thr Leu His Asp Ala Pro Val Arg Ser ... Ser end FIG. 10  pDP516-16
```

HIGH LEVEL EXPRESSION IN *E. COLI* OF SOLUBLE MATURE HIL-1BETA AND DERIVATIVES WITH ALTERED BIOLOGICAL ACTIVITY

CROSS-REFERENCE

This application is a continuation-in-part of co-pending application Ser. No. 006,870, filed Jan. 27, 1987, now abandoned.

FIELD OF THE INVENTION

The invention relates to expression of soluble recombinant proteins corresponding to mature human interleukin 1β (hIL-1β) and derivatives of mature hIL-1β (muteins) having amino acid substitutions and insertions at the N-terminus and concomitant altered biological activities. More particularly, the invention relates to high-level expression in *E. coli* of such proteins utilizing a plasmid vector containing a lac promoter.

BACKGROUND

Human interleukin-1β (hIL-1β) is produced by stimulated monocytes initially as a 269 amino acid protein with Mr of 30,747. It is proteolytically converted to a biologically active form consisting of the 153 amino acid carboxy-terminal portion from position 117 to position 269, with Mr of 17,377. The 269 amino acid protein is referred to as pro hIL-1β; the 153 amino acid protein is referred to as mature hIL-1β.

European Patent Application Publication Number 0165654, filed by Immunex Corporation in March 1985, discloses expression of recombinant mature hIL-1β having a methionine residue preceding position 1 (met hIL-1β). Although the gene encoding hIL-1β was amplified in *E. coli*, it was expressed in yeast. In June 1985 researchers at Immunex published a paper (March et al., *Nature* 315:641–647, June 20, 1985) describing expression in *E. coli* of recombinant mature met hIL-1β using a vector containing the λ phage $P_L$ promoter. This paper states at pages 644–5 that the cells produced high levels of IL-1 activity. There is no disclosure of purification of the protein. In 1986 researchers at Immunex published another paper (Kronheim et al., *Biotechnology* 4:1078–1082, December 1986) indicating at page 1080 that the "preliminary constructions" described in the March et al. paper did not produce high levels of recombinant hIL-1β, and that purified hIL-1β had been obtained previously only from human monocytes. The Kronheim et al. paper describes high-level expression of hIL-1β in *E. coli*, using expression system pLNIL1β, also containing the λ phage $P_L$ promoter, and purification of the protein.

European Patent Application Publication Number 0161901 and Auron et al. *Proc. Natl. Acad. Sci. USA* 81:7907–7911 (1984) disclose cloning vehicles containing the nucleotide coding sequence for pro hIL-1β (pcD415 and pcD1218) and various fragments thereof. EPA Publication Number 0161901 states that the sequences can be fused into an expression vector and expressed in either eukaryotic or prokaryotic cells, but does not disclose a specific expression system. Dinarello et al. *J. Clin. Invest.* 77:1734–1739 (June 1986) discloses expression in *E. coli* of a protein consisting of amino acids 71–269 of pro hIL-1β preceded by 24 amino acids contributed by the expression vector, followed by enzymatic digestion to produce a protein consisting of amino acids 112–269 of pro hIL-1β. The paper states that the expression vector was constructed by inserting a fragment of pcD1218 into an *E. coli* expression plasmid, which is not further identified. Rossenwasser et al., *Proc. Natl. Acad. Sci. USA*, 83:5243–5246 (July 1987) discloses expression in COS monkey cells of pro hIL-1β using plasmids pcD415 and 1218, and various deleted forms, including one consisting of about 136 amino acids of the carboxy terminal of mature hIL-1β.

Pro human interleukin 1α (pro hIL-1α) is a 271 amino acid protein with about 27% homology to pro hIL-1β. It is processed proteolytically to a biologically active 17 approximately kD protein consisting of the 159 amino acids of the carboxy-terminal of pro hIL-1α. Gubler et al., *J. Immunology* 136:2492–2497 (1986) discloses expression in *E. coli* of the carboxy-terminal 154 amino acids of pro hIL-1α, using a plasmid containing the λ phage $P_L$ promoter.

Plasmid vectors containing lac promoters such as pUC8 have been described (Vieira and Messing et al., *Gene* 19:259–268 (1982)) and are available commercially from Pharmacia, Piscataway, NJ and Bethesda Research Laboratory, Bethesda MD. EPA Publication 0161901 and the Rossenwasser et al. publication cited above mention pUC8 in connection with construction of cloning and expression vectors, but only as a source of a polylinker fragment used in constructing plasmid pcD1218.

SUMMARY OF THE INVENTION

We have discovered that insertion into plasmid pUC8 of DNA coding for mature hIL-1β, or a derivative of mature hIL-1β with amino acid substitution or insertion at one or more of positions 1 to 4, in such a way that an ATG/Met/start codon downstream from the lac promoter of pUC8 is separated from the TCA/Ser codon for position 5 of mature hIL-1β by 4 to 18 codons, provides a plasmid which is capable of high level expression in *E. coli* of soluble protein containing the amino acid sequence of mature hIL-1β or the derivative of hIL-1β.

We have found that derivatives of hIL-1β containing amino acid alterations within the N-terminal sequence of mature hIL-1β exhibit varying degrees of biological activity. The specific biological activities of the altered forms of hIL-1β constructed ranged from an increase of approximately 7-fold to a decrease of approximately 700-fold, relative to mature hIL-1β. These results show that the structure of the N-terminal sequence of mature hIL-1β is critical for the biological function of the molecule. The present results identify the N-terminal sequence of mature hIL-1β, specifically the N-terminal 4 amino acid residues, as a target for further structural changes that may result in either an increase or decrease in the biological activity of the molecule. Thus, it is demonstrated that changes in the N-terminal sequence of mature hIL-1β can be used to modulate the biological activity of hIL-1β.

The IL-1β derivatives of this invention with biological activity greater than about 10% that of native hIL-1β can be used in the same way that native and recombinant hIL-1β are used, e.g., to stimulate hematopoiesis (Oppenheim et al., *Immunology Today* 7: 45–56 (1986); Dinerello, *Bull. Inst. Pasteur* 85: 267–185 (1987)). The IL-1β derivatives of this invention which have biological activity less than about 10% that of native hIL-1β have utility as research tools, e.g., as negative controls in assays of IL-1 biological activity.

The proteins produced by this invention are soluble. When E. coli cells expressing the proteins are lysed by sonication and centrifuged, the proteins are found in the supernatant liquid, not in the pellet. Because of this, the proteins can be readily purified to homogeneity in a functional conformation.

Plasmids of this invention in E. coli strain JM 101 have been deposited in the American Type Culture Collection (ATCC) 12301 Parklawn Drive, Rockville, MD, USA, in accordance with the provisions of the Budapest Treaty on Deposit of Microorganisms. Deposited plasmids and their ATCC accession numbers are:

| Plasmid | ATCC NO. |
|---|---|
| pDP506 | 67302 |
| pDP516 | 67303 |
| pD516-22a | 67304 |
| pD516-18 | 67305 |

FIGS. 5 to 8 indicate the DNA sequences of the above plasmids and the amino acid sequences of the proteins which they express. FIGS. 9 and 10 indicate the DNA sequences of two other plasmids of the invention, pDP516-23 and pDP516-16, and the amino acid sequences of the proteins which they express. The numbers 1 and 117, in FIGS. 3 and 5 to 10 indicate position 1 at the amino terminal of mature hIL-1β, which corresponds to position 117 of pro hIL-1β. The numbers 153 and 269 indicate position 153 at the carboxy terminal of mature hIL-1β, which corresponds to position 269 of pro hIL-1β.

Plasmid pDP506 was prepared by inserting a HgiAI to PstI DNA fragment encoding amino acid sequence 116 to 269 of pro hIL-1β into the PstI site of pUC8. Plasmids of the pDP516 series were produced by digesting pDP506 with EcoRI and SalI to produce linear DNA, digesting the linear DNA with Bal 31 exonuclease, filling in the 3' recessed ends by Klenow reaction, and ligating the blunt ends with T4 DNA ligase to recircularize the DNA. Other plasmids of this invention were also produced from pDP506, as described below.

E. coli cells of strain JM 101 were transformed with the plasmids and the cells were cultured to express the proteins. The cells were sonicated, the lysate was centrifuged, and the supernatant was subjected to anion exchange and sizing column chromatography to purify the proteins to homogeneity.

Table I lists some plasmids of this invention and gives the amino acid sequences of the proteins they express, using single letter symbols to represent amino acid residues as described in Lehninger, Biochemistry, Second Edition, p. 72, Worth Publishers, Inc. (1975).

TABLE 1

| Recombinant Plasmid | hIL-1β-derived protein | 113 | 114 | 115 | 116 | 117 / 1 | 118 / 2 | 119 / 3 | 120 / 4 | 121 ... 269 / 5 ... 153 |
|---|---|---|---|---|---|---|---|---|---|---|
| phIL-1β | hIL-1β | | | | | A | P | V | R | S ... S |
| pDP-516 | DP-516 | | | $\underline{T}$ | $\underline{N}$ | A | P | V | R | S ... S |
| pDP-516-22a | DP-516-22a | | | | | $\underline{T}$ | P | V | R | S ... S |
| pDP-516-18 | DP-516-18 | | | | | $\underline{T}$ | $\underline{M}$ | V | R | S ... S |
| pDP-516-23 | DP-516-23 | | | $\underline{I}$ | $\underline{N}$ | A | P | V | R | S ... S |
| pDP-516-16 | DP-516-16 | $\underline{T}$ | $\underline{L}$ | $\underline{H}$ | $\underline{N}$ | A | P | V | R | S ... S |
| pGly-3 | Gly-3 | | | | | $\underline{T}$ | $\underline{M}$ | $\underline{G}$ | R | S ... S |
| pPro-3 | Pro-3 | | | | | $\underline{T}$ | $\underline{M}$ | $\underline{P}$ | R | S ... S |
| pLeu-3 | Leu-3 | | | | | $\underline{T}$ | $\underline{M}$ | $\underline{L}$ | R | S ... S |
| pIle-3 | Ile-3 | | | | | $\underline{T}$ | $\underline{M}$ | $\underline{I}$ | R | S ... S |
| pThr-3 | Thr-3 | | | | | $\underline{T}$ | $\underline{M}$ | $\underline{T}$ | R | S ... S |
| pGlu-4 | Glu-4 | | | | | $\underline{T}$ | $\underline{M}$ | $\underline{V}$ | $\underline{E}$ | S ... S |
| pTyr-4 | Tyr-4 | | | | | $\underline{T}$ | $\underline{M}$ | V | $\underline{Y}$ | S ... S |
| pLys-4 | Lys-4 | | | | | $\underline{T}$ | $\underline{M}$ | V | $\underline{K}$ | S ... S |

The N-terminal sequences of mature hIL-1β and several derivatives of hIL-1β are indicated in Table 1. The hIL-1β-derived proteins were expressed in E. coli using the plasmid expression vectors indicated in Table 1. The hIL-1β-derived proteins expressed in E. coli contain an N-terminal Met residue (not shown) preceding the sequence indicated in Table 1, that may be removed in E. coli by the action of aminopeptidases. The amino acids present in the derivatives of hIL-1β that differ from the sequence of authentic, mature hIL-1β are underlined in Table 1. The numbers in the two horizontal rows indicate the amino acid residue numbers of pro-hIL-1β (upper row) and mature hIL-1β (lower row) The dots indicate the normal amino acid residues between positions 121 and 269 of pro hIL-1β which correspond to positions 5 and 153 of mature hIL-1β.

DETAILED DESCRIPTION

Construction of pDP506

Referring to FIGS. 1 and 2, starting material for preparation of plasmid pDP506 was plasmid pcD1218, which is described in the EPA Publication No. 0161901 and the Auron et al. and Rossenwasser et al. publications, cited above. A 1.6 kilobase pair (Kb) segment (horizontal line, FIG. 2) containing DNA coding for pro hIL-1β was cut from pcD1218 by BamHI digestion. FIG. 2 indicates by vertical lines restriction sites in the 1.6 Kb segment, as well as the sites at 1, 348/351 and 807 nucleotides corresponding to the amino- and carboxy-terminals of pro and mature hIL-1β. The 1.6 Kb segment was subcloned into the BamHI site of plasmid pUC9 (available from BRL and Pharmacia) to produce hybrid plasmid pUC9-pro hIL-1β. Plasmid pUC9-pro hIL-1β contains two AccI sites. A 0.5 Kb non-coding region from the AccI site in the 1.6 Kb pcD1218-derived fragment (FIG. 2) to the AccI site in pUC9 was deleted by digestion of pUC9-pro hIL-1β with AccI, followed by ligation to generate plasmid pUC9-pro hIL-1βΔAccI which was used to amplify in E. coli the DNA coding for pro hIL-1β.

FIG. 3 shows the nucleotide sequence coding for amino acid positions 112 to 269 of pro hIL-1β, and indicates the PstI restriction site present in pUC9-pro hIL-1βΔAccI approximately 150 nucleotides downstream from the pro hIL-1β coding sequence, as well as the HgiAI site at the codon for positions 114 and 115. The horizontal and vertical lines in FIGS. 3 to 5 indicate the sequence recognized and cut by the indicated restriction endonuclease.

To construct pDP506, a 0.6 Kb restriction fragment was produced by digestion of pUC9-pro hIL-1βΔAccI with HgiAI and PstI, and the 0.6 Kb fragment containing the mature hIL-1β coding sequence was inserted into the PstI site of pUC8. FIG. 4 shows that portion of pUC8 which includes the PstI site and the upstream ATG/Met/start codon separated from that site by 11 amino acid codons. Although the recognition sites of HgiAI and PstI are different, the 3' protruding ends produced by the enzymes are identical, so an HgiAI end can be ligated to a PstI end with T4 DNA ligase, resulting in a sequence not recognized by either enzyme.

As shown in FIG. 5, pDP506 contains the coding sequence for amino acid positions 115 to 269 of pro hIL-1β preceded by 13 codons of pUC8. The ATG/-Met translation start codon from pUC8 is separated from the codon for position 3 (Val) of hIL-1β by 16 amino acid codons.

Construction of pDP516, pDP516-16, -18, -22a and -23

The construction of pDP506, pDP516, pDP516-16, -18, -22a, and -23 is outlined schematically in FIG. 1. Plasmid pDP506 was digested with EcoRI and SalI and this linear DNA was subjected to digestion with Bal 31 exonuclease for about 10 to 15 seconds to remove nucleotides from both ends of both strands. At the end of this digestion, recessed 3' ends were filled in by Klenow reaction, then the resulting blunt ends were ligated with T4 DNA ligase to recircularize the DNA. This resulted in production of a pool of plasmids, later identified by protein expression analysis and DNA sequencing as including pDP516, pDP516-16, -18, -22A and 23.

As indicated in FIG. 5, pDP506 contains SmaI and BamHI sites in the region contributed by pUC8, and these also can be used to provide plasmids of this invention. Also, it is expected that certain other plasmids containing lac promoters, such as pUC12, could be used to produce plasmids of this invention.

All DNA manipulations described herein were carried out with reagents and under conditions described in Maniatis et al., *Molecular Cloning, A Laboratory Manual*, Cold Spring Harbor Laboratory, New York (1982).

Construction of Plasmids pDP506ΔPst, phIL-1 β, pGly-3, pPro-3, pLeu-3, pThr-3, pIle-3, pGlu-4, pTyr-4, and pLys-4

Plasmid pDP506 contains two HindIII sites. One HindIII site is within the hIL-1β coding sequence. This site includes codon 133 of pro hIL-1β, which corresponds to codon 16 of mature hIL-1β. The other HindIII site is adjacent to the PstI site within the pUC8-derived segment of pDP506, downstream (3') of the hIL-1β coding sequence. The pUC8-derived HindIII site in pDP506 was deleted using the following procedure to yield pDP506ΔPst. Plasmid pDP506 was digested with PstI and Bal31 and ligated. The exonuclease removed about 75 base pairs around the PstI site. Therefore, it also deleted the adjacent HindIII site. The resulting plasmid was designated pDP506ΔPst. Plasmid pDP506ΔPst was digested with EcoRI and HindIII and the EcoRI to HindIII oligonucleotide was replaced with a 73 base pair EcoRI to HindIII oligonucleotide with coding strand: (A A T T C C A T A G A G G G T A T T A C A T A T G G C A C C T G T A A G A T e,uns/C/ T C T G A A C T G C A C G C T C C G G G A C T C A C A G C A A A A A) to produce plasmid phIL-1β which codes for mature form of hIL-1β. The 73 base pair oligonucleotide includes a ribosome binding site (dashed underline), translation initiation codon ATG (underlined) and a BglII restriction site (underlined), which does not occur naturally in the IL-1β coding sequence, but was introduced without changing the amino acid composition at positions 4 and 5 of hIL-1β.

A series of 35 base pair oligonucleotides (from EcoRI to BglII) were made, with proper coding sequence altered and used to replace the 35 base pair EcoRI to BglII segment of phIL-1β to generate various derivatives of hIL-1β with amino acid substitutions within the N-terminus. The plasmid expression vector designation, hIL-1β-derived protein designation, and N-terminal sequence of the hIL-1β derivatives produced are given in Table 1.

Transformation, Expression and Purification

*E. coli* cells of the ampicillin-sensitive JM 101 strain were transformed with plasmid DNA. Cells were grown in L Broth supplemented with ampicillin, (100 μg/ml) and IPTG (isopropeylthio-β-galactoside at 37° C. in a rotary shaker (150 rpm). Recombinant clones were grown to a Klett reading of 30 (determined by Klett-Summerson Photoelectric Colorimeter, Klett Manufacturing Company, New York) at which time IPTG was added to a final concentration of 1 mM. Cells were harvested at various time points for further characterization. Cells from 500 ml culture were harvested, resuspended in 50 ml of sonication buffer (50 mM Tris pH 8.0, 1 mM EDTA, 1 mM DTT) and sonicated for 7 to 10 seconds in a 5 ml volume. Sonicated samples were centrifuged for 5 minutes at 4° C. The supernatants and pellets were kept separate. Sonicated lysate was filtered with a Millipore filter (0.45μ) before it was applied to SYNCHROPAK Ion Exchange Column (2.1×25 cm) from Synchrom, Inc., Linden, Ind. The hIL-1β containing fractions in this and subsequent chromatography steps were identified by Western Blot assay using a rabbit polyclonal antibody against monocyte hIL-1β. Fractions containing hIL-1β were pooled and concentrated to 1 to 3 ml by ultrafiltration with an AMICON concentrator and were further purified by ACA sizing column chromatography (2.4×100 cm) from LKB Instruments, Inc., Gaithersburg, MD. Buffer used in both columns was 50 mM Tris pH 8, 1 mM EDTA, 1 mM DTT. Native form hIL-1β was purified from the myeomonocytic THP-1 cell line as described by Matsushima et al. *Biochem.* 25:3424–3429 (1986).

For gel analysis, samples were diluted in a Laemmli sample buffer (Gubler et al. *J. Immunol.* 136:2492–2497 containing 1 mM DTT and boiled for three minutes before being applied to a SDS-PAGE vertical slab gel (BioRad and Hoeffer apparatus) containing 15% acrylamide or a 8 to 25% gradient acrylamide gel using the Pharmacia phast gel system. Gels were stained with Coomassie blue and the molecular weight of a recombinant hIL-1β was calculated by linear regression analysis using molecular weight standards (BRL prestained or Pharmacia molecular weight markers).

Western Blot analyses were carried out as described in Towbin et al. *Proc. Natl. Acad. Sci. USA* 76:4350–4356. Briefly, *E. coli* proteins were separated by SDS-PAGE and transblotted onto 0.45 mm transblotted proteins on the nitrocellulose paper. The nitrocellulose papers were reacted with rabbit anti-hIL-1β antibodies and the immunoreactive recombinant hIL-1β bands were revealed by incubating with horseradish peroxidase conjugated goat anti-rabbit IgG antibodies (BioRad, Richmond, CA).

Colonies of cells transformed with plasmids of the pDP516 series were individually picked and grown overnight in 1 ml of L Broth supplemented with ampicillin and lac inducer IPTG. Following overnight growth, 0.5 ml of each cell culture was centrifuged, resuspended in protein lysing buffer and subjected to SDS-PAGE. Transformants that exhibited high level expression of hIL-1β with apparent molecular weight approximately equal to that of pDP516 were selected. Plasmid DNA from each individual identified clone was isolated and sequenced and the recombinant hIL-1β was purified as described above.

When cells carrying recombinant plasmids pDP506 and the plasmids of the pDP516 series were grown in the presence of IPTG, recombinant hIL-1β became the major product (15 to 30% by weight) of total cellular protein after 4 hours of induction. When the soluble IL-1-derived proteins were chromatographed using the SYNCHROPAK anion exchange column the IL-1 derived protein eluted predominantly in the flowthrough i.e. the major peak of non-retained from a SYNCHROPAK anion exchange column. The hIL-1β containing fractions present in the peak were pooled. The purity was greater than 95% as judged by SDS-PAGE and by Western Blot analysis. The pooled fractions were further purified by ACA sizing column purification. Recombinant hIL-1β proteins were shown to be greater than 99% pure following this step. After the above chromatgraphic steps the endotoxin concentration of the proteins was less than 3 ng/mg of hIL-1β protein.

The identity of the recombinant plasmids was determined by DNA sequencing. Direct plasmid sequencing was carried out by the procedure described in Chen et al. DNA 4:165–170. A synthetic 16-mer oligonucleotide (GTGGAATTGTGAGCG) was used as a primer. The identity of the recombinant proteins was confirmed by amino acid composition and sequencing of the amino terminal 24 amino acids. Purified protein was analyzed on a Beckman spinning cup sequencer model 890M.

Plasmids pGly-3, pPro-3, pLeu-3, pThr-3, pIle-3, pGlu-4, pTyr-4, and pLys-4 were used to transform E. coli and the corresponding proteins were expressed and purified in the same manner as described above.

Bioactivity

Purified recombinant hIL-1β proteins were evaluated by the standard murine thymocyte (C3H/HeJ mice) proliferation as described in Lachman et al. *Meth. in Enzymol.* 116:467–479 and the standard Gingival Fibroblast Prostaglandin $E_2$ ($PGE_2$ production assay) ($PGE_2$ RIA kit NEN Research Products, E. I. du Pont de Nemours and Company, N. Billerica, MA). The biological activity of DP506 is about 10% of that of native hIL-1β derived from THP-1 cell line. The bioactivity of DP516, DP516-16 and DP516-23 is approximately equal to or better than that of native hIL-1β.

Table 2 shows the biological activity in one test of hIL-1β, DP516-22a, DP516-18, and Glu-4 determined by the thymocyte proliferation assay. DP516-22a which has the substitution alanine to threonine at the N-terminus of IL-1, shows approximately a 4-fold increase in bioactivity. Another mutant, DP516-18, which has the first two amino acids replaced, demonstrated approximately 7-fold enhanced activity.

TABLE 2

Bioactivity of *E. coli*-expressed Derivatives of hIL-β with Altered N-terminal Sequences

| Protein Designation | N-terminus Sequence | Specific Activity[a] (Units/mg) | Relative Specific Activity (%) |
|---|---|---|---|
| hIl-1β[b] | Ala—Pro—Val—Arg—Ser—Leu— | $1.0 \pm 1.0 \times 10^7$ | 100 |
| DP516-22a | Thr—Pro—Val—Arg—Ser—Leu— | $3.8 \pm 1.1 \times 10^7$ | 380 |
| DP516-18 | Thr—Met—Val—Arg—Ser—Leu— | $7.0 \pm 1.5 \times 10^7$ | 700 |
| Glu-4 | Thr—Met—Val—Glu—Ser—Leu— | $1.4 \pm 1.2 \times 10^4$ | 0.14 |

[a]Purified proteins were analyzed by the thymocyte proliferation assay. One unit equals the amount of material which gives half of the maximum stimulation. Values are mean ± SEM from 5 independent experiments and are normalized against mature monocyte hIL-1β.
[b]Native mature hIl-1β derived from monocyte cell line THP-1.

Examination of the N-terminal sequence of hILl-1β suggested that a protonated arginine residue at position 4 of IL-1β might be involved in salt-bridge formation or hydrogen bonding and play a role in stabilizing the active conformation of the protein. Substitution of arginine by glutamic acid (Glu-4), which is a single amino acid replacement compared to DP516-18, resulted in a decrease of specific bioactivity of approximately 700- to 7000-fold. This result shows that the positively charged arginine residue at position 4 is critical for the biological activity of hIL-1β. Substitution of Arg in position 4 with Lys, as in Lys-4, resulted in approximately no change in the specific biological activity of the hIL-1β-derived protein.

Substitution of Arg at amino acid position 4 with a Tyr residue, as in hIL-1β derivative Tyr-4, resulted in a decrease in specific biological activity of approximately 10-fold. These results are shown in Table 3, where N indicates the number of tests utilizing the thymocyte proliferation assay.

TABLE 3

| E. coli-expressed protein | N | Average Specific Activity (Units/mg)[a] | Standard Error | Relative Specific Activity[b] (%) |
|---|---|---|---|---|
| hIL-1β | 6 | $2.79 \times 10^7$ | $0.81 \times 10^7$ | 279 |
| DP516-18 | 14 | $6.67 \times 10^7$ | $1.39 \times 10^7$ | 667 |
| DP516-22a | 3 | $2.98 \times 10^7$ | $0.53 \times 10^7$ | 298 |
| Glu-4 | 6 | $1.83 \times 10^3$ | $0.67 \times 10^3$ | 0.018 |
| Lys-4 | 5 | $1.80 \times 10^7$ | $0.76 \times 10^7$ | 180 |
| Tyr-4 | 3 | $1.80 \times 10^6$ | $0.17 \times 10^6$ | 18 |
| Pro-3 | 5 | $9.91 \times 10^6$ | $2.28 \times 10^6$ | 99 |
| Thr-3 | 3 | $6.10 \times 10^6$ | $5.15 \times 10^6$ | 61 |
| Ile-3 | 4 | $2.75 \times 10^7$ | $1.36 \times 10^7$ | 275 |
| Leu-3 | 4 | $2.72 \times 10^7$ | $1.74 \times 10^7$ | 272 |
| Gly-3 | 7 | $2.87 \times 10^6$ | $1.18 \times 10^6$ | 29 |

[a]One unit equals the amount of material which gives half of the maximum stimulation.
[b]Calculated from the specific activity relative to native mature hIl-1β derived from monocyte cell line THP-1.

In summary, we utilized site specific mutagenesis to engineer a series of recombinant hIL-1β analogs which have various degrees of bioactivity. Manipulation of the amino-terminal sequence of hIL-1β generated recombinant proteins that showed increased or decreased bioactivity as compared to natural hIL-1β. In particular, we have shown that the arginine at the fourth position of hIL-1β is one of the key residues in the function of hIL-1β. Substitutions engineered specifically within the N-terminal 4 amino acid residues of mature hIL-1β are demonstrated to modulate the specific biological activity of the molecule.

When the identity of DP516 was confirmed by amino acid sequencing it was found that approximately 89% of the protein molecules begin with an N-terminal threonine and approximately 11% begin with methionine, probably due to the incomplete removal of the initiation amino acid methionine by *E. coli* amino peptidases. Mixed amino termini is a common phenomenon in prokaryotic gene expression. Although FIGS. 5 to 10 and Tables 1 and 2 indicate that the recombinant hIL-1β proteins of this invention begin with threonine, a portion of the molecules can begin with methionine preceding the threonine.

It is expected that plasmid expression vectors containing a lac promoter can be used for high level expression in *E. coli* of hIL-1β substitution and deletion mutants other than those specifically described in this specification. The claims are intended to cover such equivalents.

All publications cited in this specification are incorporated herein in their entirety.

I claim:

1. Derivative of mature hIL-1β having amino acid substitutions at the first appearing contiguous Ala-Pro in the mature protein and having enhanced biological activity in comparison to native and *E. coli*-expressed mature-hIL-1β, wherein the substitutions are Thr and Met for Ala and Pro, respectively.

* * * * *